US012564677B2

(12) United States Patent
Kearns et al.

(10) Patent No.: US 12,564,677 B2
(45) Date of Patent: Mar. 3, 2026

(54) SYSTEMS AND METHODS FOR AUTOMATED INSULIN DELIVERY RESPONSE TO INACCURATE OR MISSED GLUCOSE VALUES

(71) Applicant: Tandem Diabetes Care, Inc., San Diego, CA (US)

(72) Inventors: Jacob Kearns, San Diego, CA (US); Michael Michaud, San Diego, CA (US); Geoffrey A. Kruse, San Diego, CA (US); Garrett Marin, San Diego, CA (US); Paul Harris, San Diego, CA (US); Thomas R. Ulrich, Oceanside, CA (US); Brendan Nichols, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 386 days.

(21) Appl. No.: 17/075,423

(22) Filed: Oct. 20, 2020

(65) Prior Publication Data

US 2021/0113766 A1     Apr. 22, 2021

Related U.S. Application Data

(60) Provisional application No. 62/923,954, filed on Oct. 21, 2019.

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 2205/18* (2013.01); *A61M 2205/3331* (2013.01); *A61M 2205/3368*
(2013.01); *A61M 2205/3584* (2013.01); *A61M 2205/42* (2013.01); *A61M 2205/505* (2013.01); *A61M 2205/52* (2013.01); *A61M 2209/01* (2013.01); *A61M 2230/201* (2013.01)

(58) Field of Classification Search
CPC ............... A61M 5/1723; A61M 5/142; A61M 5/14244; A61M 2205/18; A61M 2205/3584; A61M 2205/42; A61M 2205/505; A61M 2205/52; A61M 2230/201; A61M 2209/01; G16H 20/17
See application file for complete search history.

(56) References Cited

U.S. PATENT DOCUMENTS

| 4,191,184 A | 3/1980 | Carlisle |
|---|---|---|
| 4,619,653 A | 10/1986 | Fischell |

(Continued)

FOREIGN PATENT DOCUMENTS

| CA | 2930776 C | 5/2018 |
|---|---|---|
| WO | WO 9857683 | 12/1998 |

(Continued)

*Primary Examiner* — Dung T Ulsh
*Assistant Examiner* — Fatimata Sahra Diop
(74) *Attorney, Agent, or Firm* — Morgan, Lewis & Bockius LLP

(57) ABSTRACT

Disclosed herein are systems and methods incorporating an ambulatory infusion pump and a CGM. These systems that can include software and related methods to provide improved automated insulin delivery algorithms that enable the algorithms to safely continue delivering insulin for some time periods of missing or known inaccurate glucose values.

21 Claims, 5 Drawing Sheets

(56) References Cited

U.S. PATENT DOCUMENTS

| | | | |
|---|---|---|---|
| 4,808,167 A | 2/1989 | Mann et al. | |
| 5,108,363 A | 4/1992 | Tuttle et al. | |
| 5,304,126 A | 4/1994 | Epstein et al. | |
| 5,358,489 A | 10/1994 | Wyrick | |
| 5,429,602 A * | 7/1995 | Hauser | A61M 5/1413 |
| | | | 604/65 |
| 5,460,605 A | 10/1995 | Tuttle et al. | |
| 5,464,392 A | 11/1995 | Epstein et al. | |
| 5,688,232 A | 11/1997 | Flower | |
| 6,077,246 A | 6/2000 | Kullas et al. | |
| RE36,871 E | 9/2000 | Epstein et al. | |
| 6,364,865 B1 | 4/2002 | Lavi et al. | |
| 6,436,072 B1 | 8/2002 | Kullas et al. | |
| 6,478,771 B1 | 11/2002 | Lavi et al. | |
| 6,500,150 B1 | 12/2002 | Gross et al. | |
| 6,641,565 B1 | 11/2003 | Lavi et al. | |
| 6,645,181 B1 | 11/2003 | Lavi et al. | |
| 6,689,108 B2 | 2/2004 | Lavi et al. | |
| 6,692,456 B1 | 2/2004 | Eppstein et al. | |
| 6,723,068 B2 | 4/2004 | Lavi et al. | |
| 6,770,054 B1 | 8/2004 | Smolyarov et al. | |
| 6,824,529 B2 | 11/2004 | Gross et al. | |
| 6,843,782 B2 | 1/2005 | Gross et al. | |
| 6,958,691 B1 | 10/2005 | Anderson et al. | |
| 6,981,499 B2 | 1/2006 | Anderson et al. | |
| 7,107,706 B1 | 9/2006 | Bailey, Sr. et al. | |
| 7,250,037 B2 | 7/2007 | Shermer et al. | |
| 7,252,651 B2 | 8/2007 | Haider et al. | |
| 7,497,827 B2 | 3/2009 | Brister et al. | |
| 7,547,281 B2 | 6/2009 | Hayes et al. | |
| 7,582,063 B2 | 9/2009 | Wurster et al. | |
| 7,621,893 B2 | 11/2009 | Moberg et al. | |
| 7,711,402 B2 | 5/2010 | Shults et al. | |
| 7,766,873 B2 | 8/2010 | Moberg et al. | |
| 7,785,313 B2 | 8/2010 | Mastrototaro | |
| 7,837,648 B2 | 11/2010 | Blair et al. | |
| 7,905,866 B2 | 3/2011 | Haider et al. | |
| 7,933,780 B2 | 4/2011 | De La Huerga | |
| 7,959,608 B2 | 6/2011 | Nash et al. | |
| 7,988,663 B2 | 8/2011 | Schiller et al. | |
| 7,998,111 B2 | 8/2011 | Moberg et al. | |
| 8,062,257 B2 | 11/2011 | Moberg et al. | |
| 8,065,096 B2 | 11/2011 | Moberg et al. | |
| 8,182,447 B2 | 5/2012 | Moberg et al. | |
| 8,257,300 B2 | 9/2012 | Budiman et al. | |
| 8,267,893 B2 | 9/2012 | Moberg et al. | |
| 8,287,495 B2 | 10/2012 | Michaud et al. | |
| 8,311,749 B2 | 11/2012 | Brauker et al. | |
| 8,369,919 B2 | 2/2013 | Kamath et al. | |
| 8,444,592 B2 | 5/2013 | Williams et al. | |
| 8,454,576 B2 | 6/2013 | Mastrototaro et al. | |
| 8,465,460 B2 | 6/2013 | Yodfat et al. | |
| 8,573,027 B2 | 11/2013 | Rosinko et al. | |
| 8,790,316 B2 | 7/2014 | Haueter et al. | |
| 8,986,253 B2 | 3/2015 | DiPerna | |
| 9,381,297 B2 | 7/2016 | Brown et al. | |
| 9,486,171 B2 | 11/2016 | Saint | |
| 9,669,160 B2 | 6/2017 | Harris | |
| 9,833,177 B2 | 12/2017 | Blomquist | |
| 9,867,937 B2 | 1/2018 | Saint et al. | |
| 9,867,953 B2 | 1/2018 | Rosinko | |
| 10,016,561 B2 | 7/2018 | Saint et al. | |
| 10,052,049 B2 | 8/2018 | Blomquist et al. | |
| 10,213,547 B2 | 2/2019 | Rosinko | |
| 10,279,106 B1 | 5/2019 | Cook et al. | |
| 10,357,606 B2 | 7/2019 | Rosinko et al. | |
| 10,357,607 B2 | 7/2019 | Blomquist et al. | |
| 10,549,051 B2 | 2/2020 | Rosinko | |
| 10,569,016 B2 | 2/2020 | Rosinko | |
| 10,864,322 B2 | 12/2020 | Saint et al. | |
| 2002/0004015 A1 | 1/2002 | Carlisle et al. | |
| 2003/0225360 A1 | 12/2003 | Eppstein | |
| 2004/0069044 A1 | 4/2004 | Lavi | |
| 2006/0173406 A1 | 8/2006 | Hayes | |
| 2006/0271022 A1 | 11/2006 | Steinbach et al. | |
| 2007/0264130 A1 | 11/2007 | Mallett | |
| 2008/0221523 A1 | 9/2008 | Moberg et al. | |
| 2008/0228056 A1 | 9/2008 | Blomquist et al. | |
| 2008/0269714 A1 * | 10/2008 | Mastrototaro | A61B 5/6849 |
| | | | 604/504 |
| 2008/0269723 A1 * | 10/2008 | Mastrototaro | A61B 5/6849 |
| | | | 604/890.1 |
| 2009/0192366 A1 | 7/2009 | Mensinger et al. | |
| 2009/0192745 A1 | 7/2009 | Kamath et al. | |
| 2010/0037680 A1 | 2/2010 | Moberg et al. | |
| 2010/0065578 A1 | 3/2010 | DiPerna | |
| 2010/0198107 A1 | 8/2010 | Groll et al. | |
| 2010/0217192 A1 | 8/2010 | Moberg et al. | |
| 2010/0217193 A1 | 8/2010 | Moberg et al. | |
| 2010/0218586 A1 | 9/2010 | Rosinko et al. | |
| 2011/0071464 A1 | 3/2011 | Palerm | |
| 2011/0130746 A1 | 6/2011 | Budiman | |
| 2011/0160654 A1 | 6/2011 | Hanson et al. | |
| 2011/0178461 A1 | 7/2011 | Chong et al. | |
| 2011/0213306 A1 | 9/2011 | Hanson et al. | |
| 2012/0330227 A1 | 12/2012 | Budiman et al. | |
| 2013/0053816 A1 | 2/2013 | DiPerna et al. | |
| 2013/0324928 A1 | 12/2013 | Kruse | |
| 2014/0180203 A1 | 6/2014 | Budiman | |
| 2014/0235981 A1 * | 8/2014 | Hayter | A61B 5/7221 |
| | | | 600/347 |
| 2014/0276419 A1 | 9/2014 | Rosinko | |
| 2016/0199571 A1 | 7/2016 | Rosinko et al. | |
| 2016/0339172 A1 | 11/2016 | Michaud et al. | |
| 2017/0000943 A1 | 1/2017 | Blomquist et al. | |
| 2017/0049957 A1 | 2/2017 | Michaud | |
| 2017/0252513 A1 * | 9/2017 | Buck, Jr. | G05B 13/024 |
| 2017/0348483 A1 * | 12/2017 | Duke | G16H 20/17 |
| 2018/0092578 A1 | 4/2018 | Blomquist | |
| 2018/0133397 A1 | 5/2018 | Estes | |
| 2018/0336208 A1 | 11/2018 | Kim | |
| 2019/0209095 A1 * | 7/2019 | Kamath | A61B 5/14532 |
| 2019/0328967 A1 | 10/2019 | Blomquist et al. | |
| 2019/0336683 A1 * | 11/2019 | O'Connor | A61M 5/145 |
| 2019/0350501 A1 | 11/2019 | Blomquist et al. | |
| 2019/0365997 A1 | 12/2019 | Harris | |
| 2019/0388015 A1 | 12/2019 | Blomquist | |
| 2020/0101226 A1 | 4/2020 | Rosinko et al. | |
| 2020/0114076 A1 | 4/2020 | Ulrich et al. | |
| 2020/0171249 A1 | 6/2020 | Rosinko | |
| 2020/0179603 A1 | 6/2020 | Rosinko | |
| 2020/0254174 A1 | 8/2020 | Kruse et al. | |
| 2020/0261649 A1 | 8/2020 | Michaud et al. | |
| 2020/0368430 A1 | 11/2020 | Ulrich et al. | |
| 2021/0001044 A1 | 1/2021 | Michaud et al. | |
| 2021/0012875 A1 | 1/2021 | Blomquist et al. | |
| 2021/0012876 A1 | 1/2021 | Blomquist | |

FOREIGN PATENT DOCUMENTS

| | | | |
|---|---|---|---|
| WO | WO 2010033634 A2 | 5/2010 | |
| WO | WO 2010099490 A2 | 9/2010 | |
| WO | WO 2012034084 A2 | 3/2012 | |

* cited by examiner

200

Receive accurate glucose levels from a CGM       202

Automatically calculate insulin doses bases on CGM data   204

Automatically delivery calculated insulin doses    206

Determine that CGM data is missing or inaccurate    208

Execute safety mechanism to continue closed loop delivery
210

Determine CGM data is accurate                212

Terminate safety mechanism
214

SYSTEMS AND METHODS FOR AUTOMATED INSULIN DELIVERY RESPONSE TO INACCURATE OR MISSED GLUCOSE VALUES

RELATED APPLICATION

The present application claims the benefit of U.S. Provisional Application No. 62/923,954 filed Oct. 21, 2019, which is hereby incorporated herein in its entirety by reference.

FIELD OF THE INVENTION

The present invention relates generally to ambulatory infusion pumps and, more particularly, to operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices that can provide continuous subcutaneous insulin injection and/or infusion therapy as an alternative to multiple daily insulin injections via syringe or injector pen. Such ambulatory infusion pumps may be worn by the user, may use replaceable medicament cartridges, and may deliver other medicaments alone, or in combination with insulin. Such medicaments include glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as continuous glucose monitoring (CGM) devices. A CGM device consists of a sensor placed under the patient's skin and affixed to the patient via an adhesive patch, a transmitter, and a monitor. A CGM device samples the patient's interstitial fluid periodically (e.g. once every 1-5 minutes) to estimate blood glucose levels over time. CGMs are advantageous because they provide more frequent insights into a user's blood glucose levels yet do not require a finger stick each time a reading is taken.

Ambulatory infusion pumps may incorporate a CGM within the hardware of the pump or may communicate with a dedicated CGM directly via a wired connection or indirectly via a wireless connection using wireless data communication protocols to communicate with a separate device (e.g., a dedicated remote device or a smartphone). One example of integration of ambulatory infusion pumps with CGM devices is described in U.S. Patent Publication No. 2014/0276419, which is hereby incorporated by reference herein. Ambulatory infusion pumps typically allow the user or caregiver to adjust the amount of insulin or other medicament delivered by a basal rate or a bolus, based on blood glucose data obtained by a CGM device, and in some cases include the capability to automatically adjust such medicament delivery. For example, based on CGM readings, some ambulatory infusion pumps may automatically adjust or prompt the user to adjust the level of medicament being administered or planned for administration or, in cases of abnormally low blood glucose readings, reducing or temporarily ceasing insulin administration.

In some cases, ambulatory insulin pumps may be configured to deliver insulin based on CGM data in a closed-loop or semi-closed-loop fashion. Some systems including these features may be referred to as automated insulin delivery (AID) systems or artificial pancreas systems because these systems serve to mimic biological functions of the pancreas for persons with diabetes.

The delivery of insulin pump therapy based on CGM readings necessitates accurate and reliable CGM data output. Some CGM devices are calibrated with blood samples to correlate actual blood glucose data with the CGM readings. These calibrations are only done periodically, such as every few days or hours (e.g., 12 hours). The longer it has been since a calibration event, the more likely the CGM data is unreliable to some degree and the more unreliable the CGM data is likely to become until the next calibration. In addition, any malfunction of the CGM sensor, loss of signal or communication with the CGM, etc., will necessarily exclude lost CGM readings from the algorithm(s) calculating pump therapy doses. Existing systems therefore generally stop automated delivery when the CGM readings are known to be inaccurate or where the readings are not received.

SUMMARY

Disclosed herein are systems and methods incorporating an ambulatory infusion pump and a CGM. These systems that can include software and related methods to provide improved automated insulin delivery algorithms that enable the algorithms to safely continue delivering insulin and/or other medicaments for some time periods of missing or known inaccurate glucose values.

In an embodiment, an ambulatory infusion pump system can include a pump mechanism configured to facilitate delivery of insulin to a user, a user interface, a communications device adapted to receive glucose levels from a continuous glucose monitor and a processor functionally linked to the pump mechanism, the user interface and the communications device. The processor can be configured to automatically calculate insulin doses with a closed loop delivery algorithm based on glucose levels received from the continuous glucose monitor and automatically deliver the insulin doses calculated by the closed loop delivery algorithm to the user with the pump mechanism. If the processor determines that glucose levels are not being received from the continuous glucose monitor or that glucose levels being received from the continuous glucose monitor are likely inaccurate, the processor can execute a safety mechanism with the closed loop insulin delivery algorithm that enables the closed loop delivery algorithm to continue to automatically calculate insulin doses for automatic delivery with the pump mechanism for a predetermined period of time while the glucose levels are not being received or the glucose levels are likely inaccurate.

In various embodiments, the safety mechanism can employ a variety of methods for safely continuing delivery of insulin and/or other medicaments during periods of inaccurate or missing glucose values, alone or in any combination with one another. Such methods can include, for example, a glucose value noise filter, comparison of a current glucose value noise to a threshold, limiting a maximum increase in an insulin delivery rate, lower an aggressiveness of the closed loop delivery algorithm, estimating inaccurate or missing glucose values based on previous or subsequent accurate values, giving less weight to known inaccurate glucose values, discarding known inaccurate glucose values, using past glucose values along with one or more physiological models to calculate insulin doses and/or reducing or delaying automatically calculated boluses and/or changes to basal delivery.

BRIEF DESCRIPTION OF THE DRAWINGS

The invention may be more completely understood in consideration of the following detailed description of various embodiments of the invention in connection with the accompanying drawings, in which.

Figure 1:
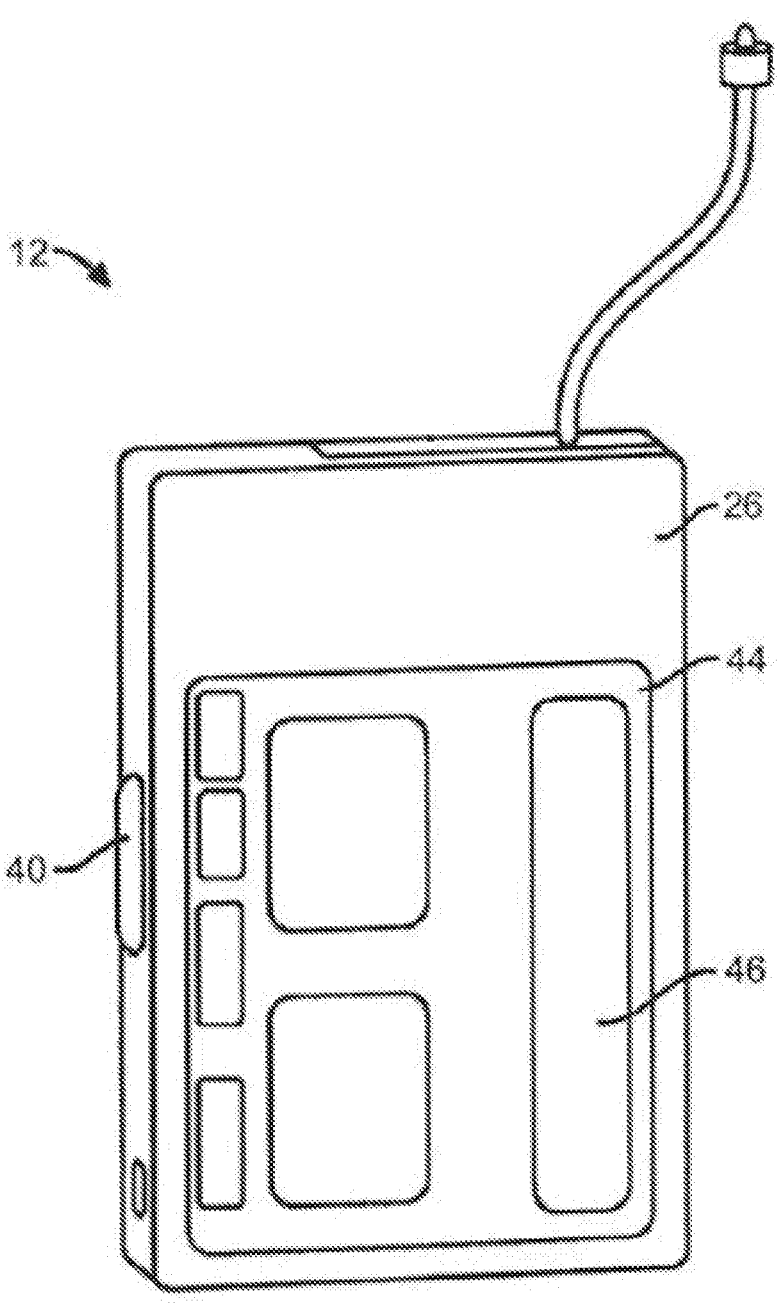
FIG. 1 is an embodiment of an ambulatory infusion pump for use with embodiments of the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an example infusion pump that can be used in conjunction with one or more embodiments of the ambulatory infusion pump system of the present disclosure. Pump 12 includes a pumping or delivery mechanism and reservoir for delivering insulin or other medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display (e.g., a dedicated remote display or a CGM display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, previously incorporated by reference above. It is to be appreciated that pump 12 may be optionally configured to deliver one or more additional or other medicaments to a patient.

Figure 2:
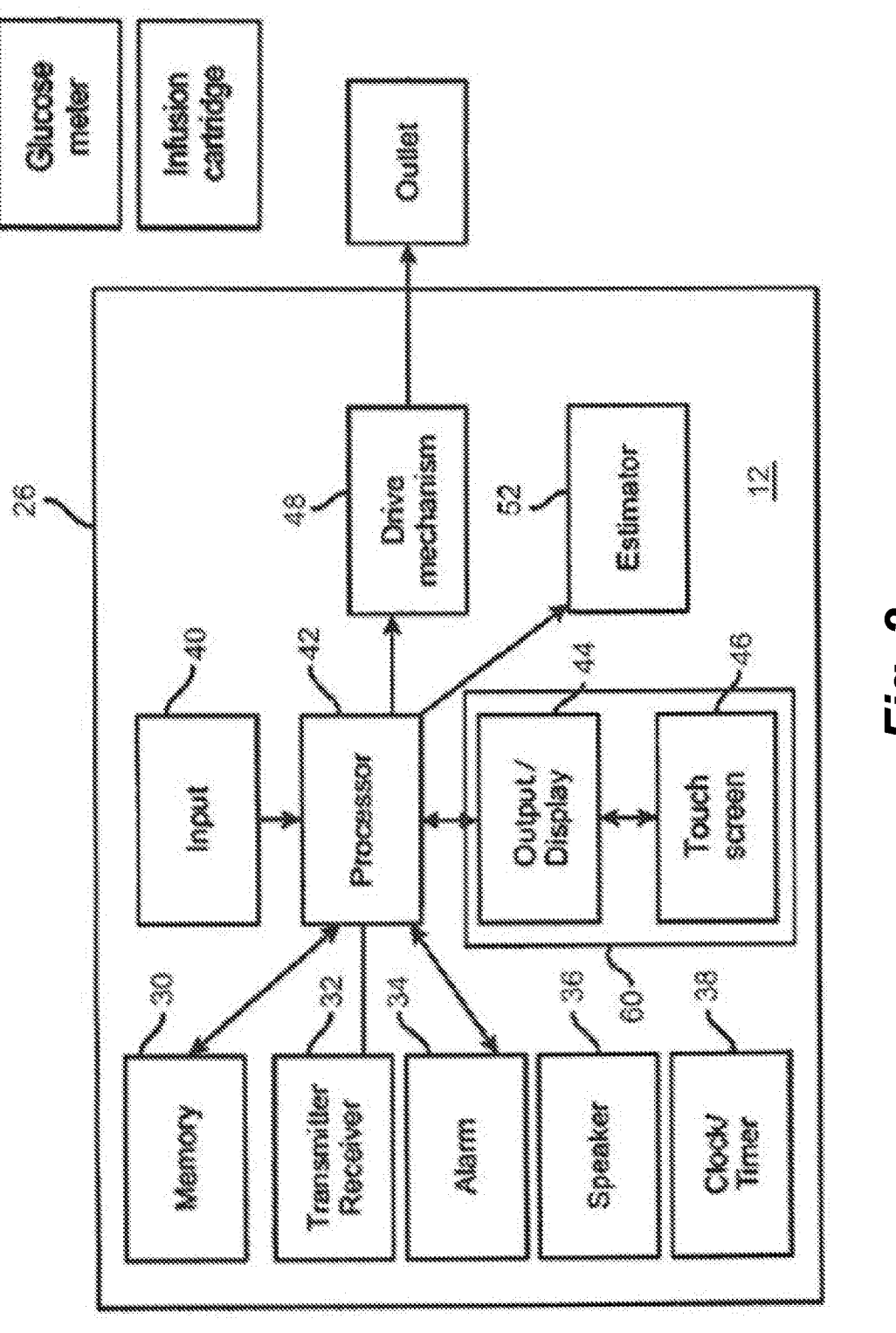
FIG. 2 is a block diagram of the ambulatory infusion pump of FIG. 1.

FIG. 2 illustrates a block diagram of some of the features that may be included within the housing 26 of pump 12. The pump 12 can include a processor 42 that controls the overall functions of the pump. The pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices through the transmitter/receiver 32 such as a remote device (e.g., CGM device), a remote control device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. The processor 42 may also include programming to receive signals and/or other data from an input device, such as, by way of example, a pressure sensor, a temperature sensor, or the like.

Figures 3A, 3B:
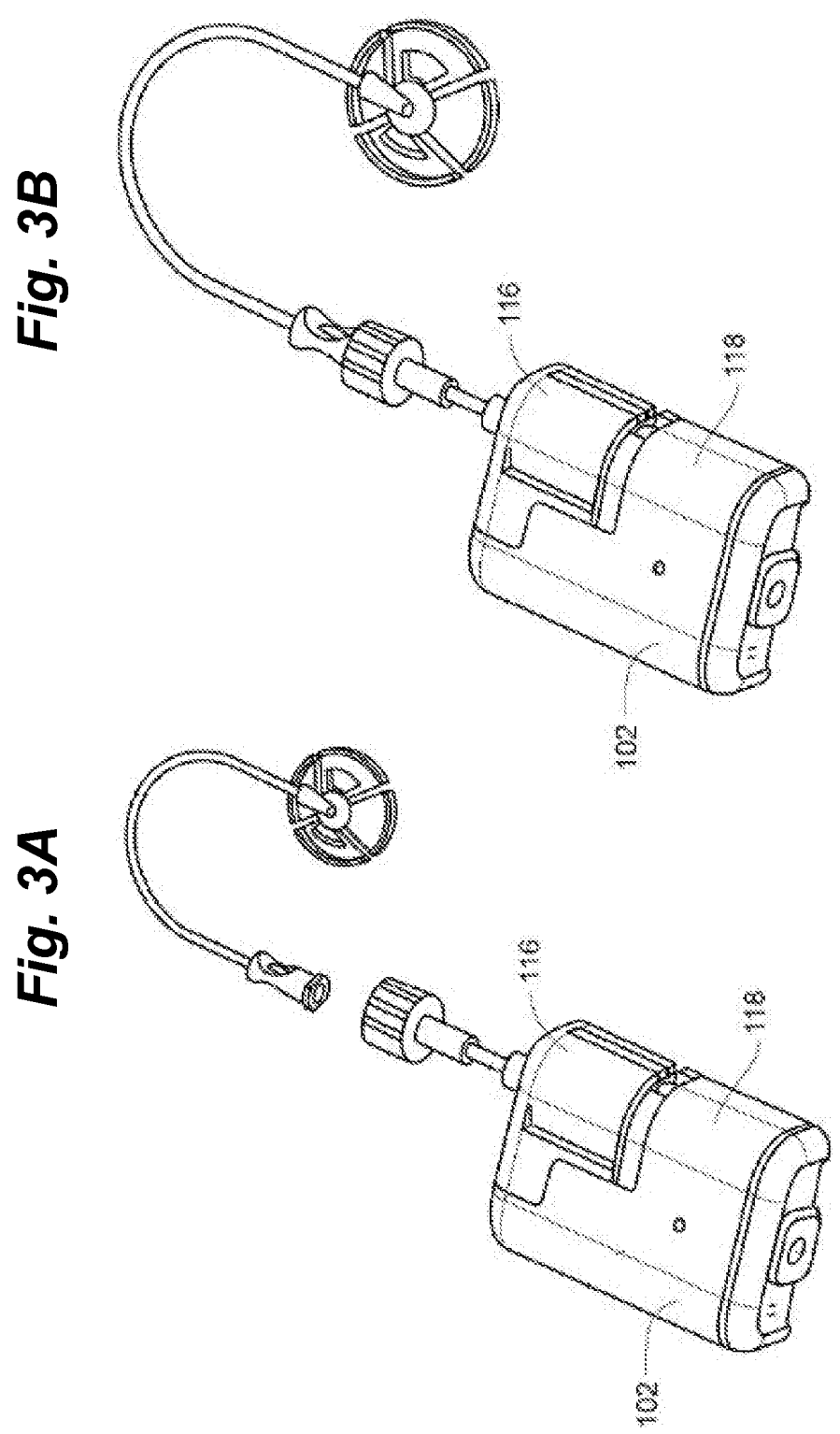
FIGS. 3A-3B are an alternate embodiment of an ambulatory infusion pump for use with embodiments of the disclosure.

FIGS. 3A-3B depicts a second infusion pump that can be used in conjunction with one or more embodiments of the ambulatory infusion pump system of the present disclosure. Pump 102 includes a pump drive unit 118 and a medicament cartridge 116. Pump 102 includes a processor that may communicate with one or more processors within the pump 102 and/or one or more processors of other devices such as a remote device (e.g., a CGM device), a remote control device, or a consumer electronic device (e.g., laptop computer, personal computer, tablet computer, smartphone, electronic watch, electronic health or fitness monitor, or personal digital assistant). The processor 42 may also include programming to receive signals and/or other data from an input device, such as, by way of example, a pressure sensor, a temperature sensor, or the like. Pump 102 also includes a processor that controls some or all of the operations of the pump. In some embodiments, pump 102 receive commands from a separate device for control of some or all of the operations of the pump. Such separate device can include, for example, a dedicated remote control device or a consumer electronic device such as a smartphone having a processor executing an application configured to enable the device to transmit operating commands to the processor of pump 102. In some embodiments, processor can also transmit information to one or more separate devices, such as information pertaining to device parameters, alarms, reminders, pump status, etc. Such separate device can include any remote display, remote control device, or a consumer electronic device as described above. Pump 102 can also incorporate any or all of the features described with respect to pump 12 in FIG. 2. In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
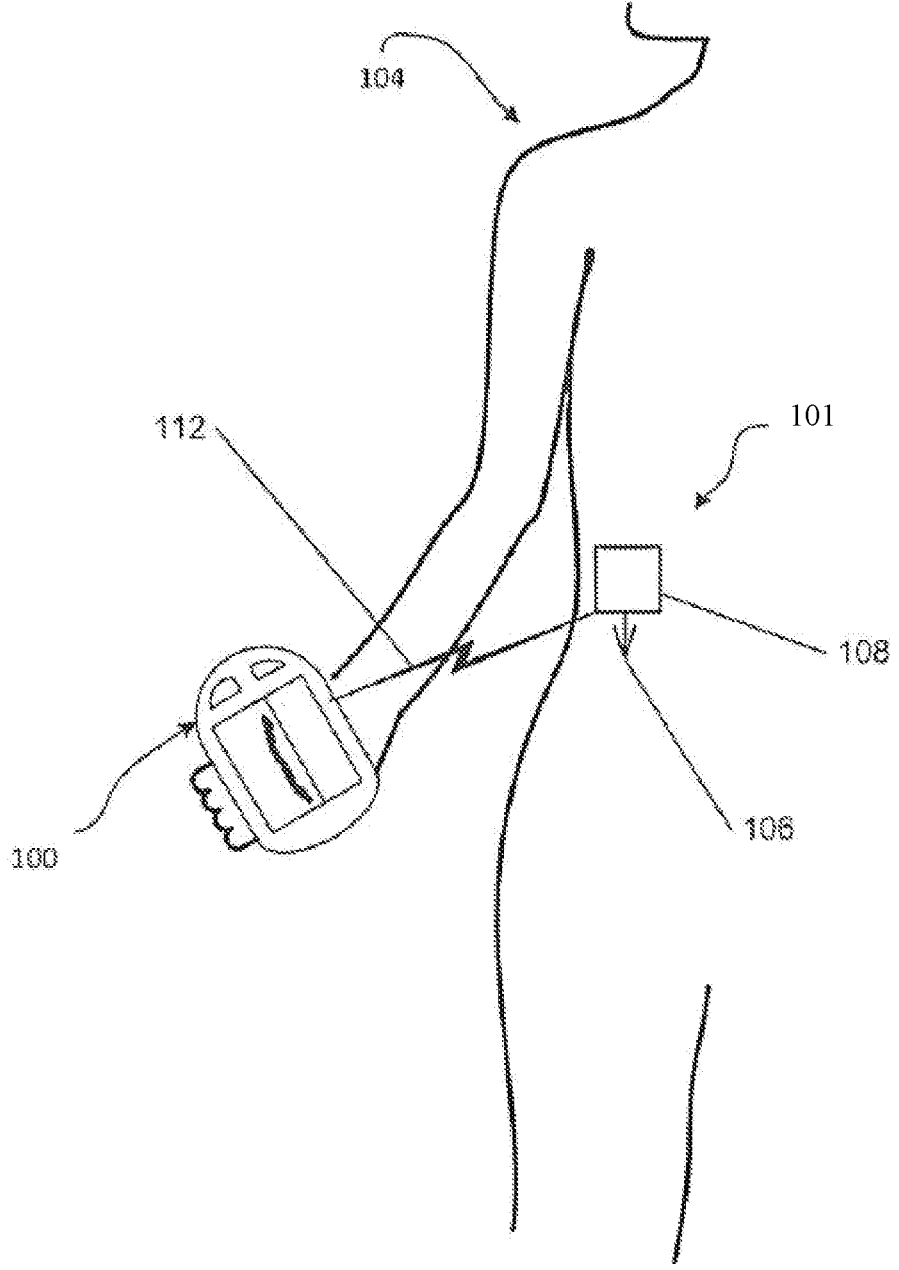
FIG. 4 is an embodiment of a CGM for use with embodiments of the disclosure.

FIG. 4 depicts an example CGM system that can be used in conjunction with one or more embodiments of the ambulatory infusion pump system of the present disclosure. The CGM system includes a sensor 101, a sensor probe 106, a sensor body 108, a receiver, and a monitor (receiver and monitor are depicted as device 100 in FIG. 4). The sensor 101 is removably affixed to a user 104 and includes a sensor probe 106 configured for transcutaneous insertion into the user 104. When placed, the sensor probe 106 reacts with the user's interstitial fluid which produces a signal that can be associated with the user's blood glucose level. The sensor 101 further includes a sensor body 108 that transmits data associated with the signal to the receiver 100 via wired or wireless connection (as represented by arrow line 112). In preferred embodiments, the receiver 100 receives the transmitted data wirelessly by any suitable means of wireless communication. By way of example only, this wireless communication may include a near field communication (NFC) radio frequency (RF) transmitter or a transmitter operating according to a "Wi-Fi" or Bluetooth® protocol, Bluetooth® low energy protocol or the like. Further detail regarding such systems and definitions of related terms can be found in, e.g., U.S. Pat. Nos. 8,311,749, 7,711,402 and 7,497,827, each of which is hereby incorporated by reference in its entirety.

With the infusion pump and CGM interfaced, the CGM can automatically transmit the CGM data to the pump. The pump can then use this data to automatically determine therapy parameters and suggest a therapy adjustment to the user or automatically deliver the therapy adjustment to the user. These therapy parameters including thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

For example, if the CGM readings indicate that the user has or is predicted to have a high blood glucose level (hyperglycemia), the ambulatory infusion system can automatically calculate an insulin dose sufficient to reduce the user's blood glucose level below a threshold level or to a target level and automatically deliver the dose. Alternatively, the ambulatory infusion system can automatically suggest a change in therapy upon receiving the CGM readings such as an increased insulin basal rate or delivery of a bolus, but can require the user to accept the suggested change prior to delivery rather than automatically delivering the therapy adjustments.

By way of further example, if the CGM readings indicate that the user has or is predicted to have a low blood glucose level (hypoglycemia), the ambulatory infusion system can, for example, automatically reduce or suspend a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the patient address the hypoglycemic condition as necessary (e.g., ingest carbohydrates), singly or in any desired combination or sequence. Such determination can be made by the infusion pump providing therapy or by a separate device that transmits therapy parameters to the infusion pump. In some embodiments, multiple medicaments can be employed in such an ambulatory infusion system as, for example, a first medicament, e.g., insulin, that lowers blood glucose levels and a second medicament, e.g., glucagon, that raises blood glucose levels.

Automated insulin delivery (AID) systems such as those described above require accurate and reliable glucose values from the CGM and therefore such systems typically terminate automated delivery for safety of the patient when the system determines that the CGM data is inaccurate or unreliable or when connectivity or other issues stop the algorithm from receiving the CGM values. Embodiments disclosed herein provide improved automated insulin delivery algorithms that enable the algorithms to safely continue delivering insulin for some time periods of missing or known inaccurate glucose values.

In embodiments, the AID algorithm can employ a glucose value noise filter based on one or more of a user's age, totally daily insulin, and weight predicted insulin action and/or response time to delay or reduce an automatically calculated correction bolus or basal rate increase. During periods of high noise, the insulin delivery may be reduced or delayed. The noise threshold at which the insulin delivery is reduced or delayed can, in some embodiments, vary based on the user's characteristics.

The current glucose level noise can also be determined based on recent glucose value readings from the CGM. If the noise is high or increased, the algorithm can reduce or delay automatic boluses and/or basal insulin delivery. In various embodiments, noise can be evaluated using variance between readings, a comparison of the variance between predicted and actual glucose values, and/or other methods.

In embodiments, future glucose levels predicted by the algorithm can be limited based on a slew rate of the electrical signal and/or a sign change of the predictor. For example, the predictor may be limited to an increase of 30 mg/dL per reading (e.g., every 5 minutes) or per a predetermined number of readings. Insulin delivery based on the predictor would therefore be reduced.

When it is known or suspected that glucose values from the CGM are lower than actual glucose levels or if the algorithm has just suspended insulin delivery due to predicted low glucose levels, in embodiments the algorithm can switch to a less aggressive mode that restricts delivery of insulin until more accurate glucose values are received. For example, automatic correction boluses may be disabled or reduced by a predetermined amount or percentage and/or basal delivery reduced in the less aggressive mode. The target glucose level or range could alternatively or additionally be increased. In some embodiments the algorithm can retain the insulin delivery changes calculated during the period of inaccuracy and either re-evaluate or use the changes in the future to make insulin delivery decisions following the period of inaccuracy. For example, if an automatic correction bolus is cancelled, it may be reapplied once accurate glucose values are received. Similarly, the algorithm can in embodiments switch to the less aggressive mode any time the glucose values are known to be inaccurate (low or high) or when glucose values have been missed and/or during periods of high noise.

In embodiments, when known inaccurate glucose values are received or glucose values are missed, the algorithm can estimate the current glucose values based on previous glucose values for a period of time (e.g., 30 minutes) using linear regression or other known prediction methods since the last known good glucose value. Various weighting methods can be used to weight the more recent glucose values more heavily in the calculation. These estimated values are used to continue automated insulin delivery over the period of time.

In some embodiments when known inaccurate glucose values are received or glucose values are missed, the algorithm can estimate the current or future glucose values based on previous glucose measures for a period time (e.g., 20 minutes). For example, a glucose value series having missing "blank" values of—101 mg/dL, 102 mg/dL, blank, blank, 103 mg/dL—can feed forward the last glucose value before the missed readings gap and use—101 mg/dL, 102 mg/dL, 102 mg/dL, 102 mg/dL, 103 mg/dL—for the purpose of continuing automated insulin delivery calculations. Similarly, the algorithm can use the subsequent values received to fill the gap. In such an embodiment, the same— 101 mg/dL, 102 mg/dL, blank, blank, 103 mg/dL—sequence can be fed back with the most recent reading to read as—101 mg/dL, 102 mg/dL, 103 mg/dL, 103 mg/dL, 103 mg/dL—for the purpose of continuing automated insulin delivery calculations. Some embodiments can use a combination of feeding forward previous values and feeding backward subsequent values.

When glucose levels are known to be inaccurate in some embodiments the algorithm can give less weight to known inaccurate values using various weighting methods. The algorithm would alter insulin delivery based on this weighting.

In embodiments, the algorithm can "bridge" accurate glucose values and discount or discard known inaccurate or missed glucose values and then use the bridges in future estimations. For example, a glucose value series having "blank" missed values of—100 mg/dL, 90 mg/dL, blank, blank, 60 mg/dL—would bridge the glucose values before and after the gap to use—100 mg/dL, 90 mg/dL, 80 mg/dL, 70 mg/dL, 60 mg/dL—to continue automated insulin delivery calculations. In one embodiment, a circular predictor buffer could be maintained and, in the case of increased sensor noise, the previous predictions could be altered based on the current state. The prediction based on this series could be used to inform the automated insulin delivery system.

When known inaccurate glucose values are received or glucose values are missed, in some embodiments the algorithm may use past glucose values along with physiological models to continue automated insulin delivery. For example, if the glucose levels are 400 mg/dL when connectivity is lost it is physiologically unlikely for the glucose values to drop down to an unsafe range without additional insulin delivery in a short period of time. In this example, increased insulin could be delivered based on the model.

It should be noted that although a number of embodiments for safely continuing delivery of insulin have been described herein, that such embodiments are not mutually exclusive. Any of the described embodiments can be used with any one or more of the other embodiments, in any combination.

Figure 5:
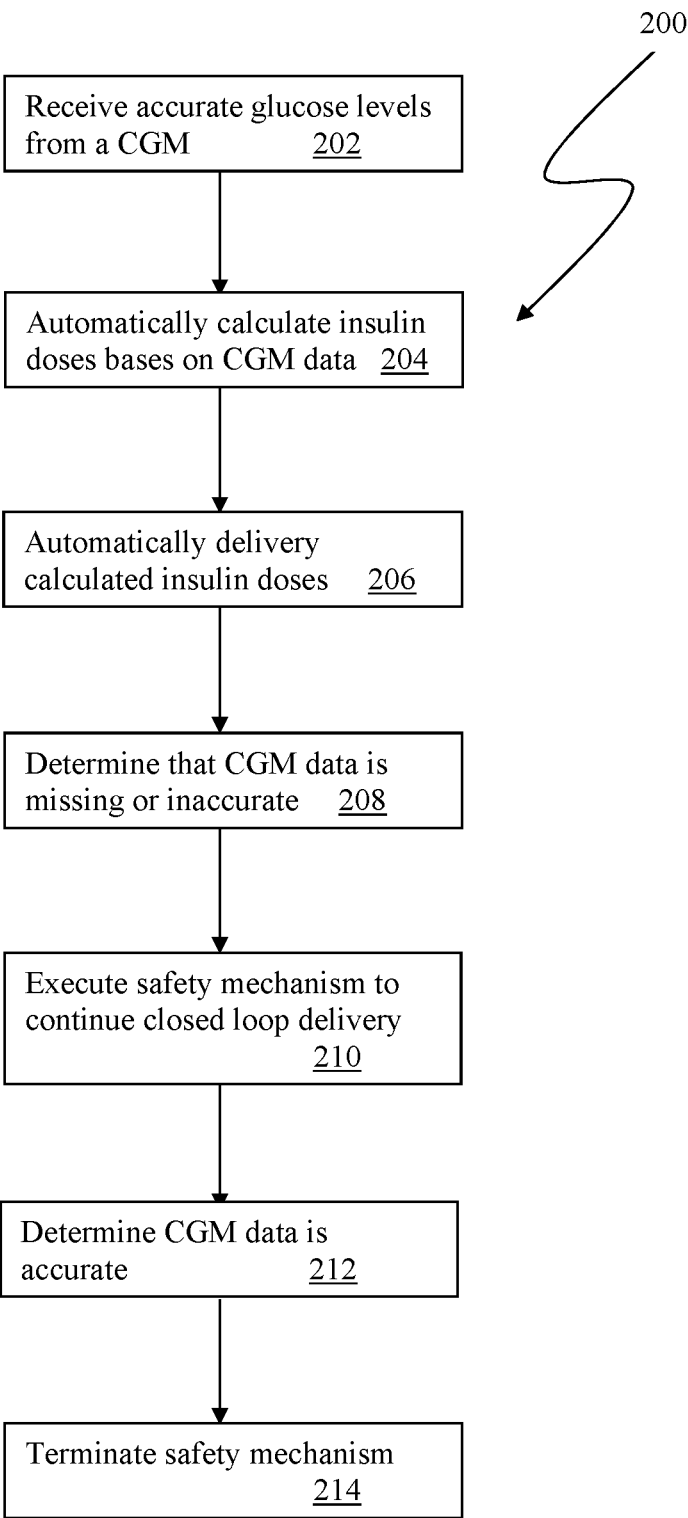
FIG. 5 is a flowchart of a method of medicament delivery utilizing a closed loop delivery algorithm according to the disclosure.

Referring now to FIG. 5, a flowchart of methods steps in a method 200 for safely delivering insulin and/or other medicaments with a closed loop delivery algorithm according to the disclosure is depicted. At step 202, the system is receiving accurate glucose levels from a CGM. The system automatically calculates insulin doses based on the CGM data at 204 and automatically delivers the calculated doses to the user at step 206. If the system determines at step 208 that the CGM is missing or inaccurate, rather than terminating or suspending the closed loop algorithm and reverting to open loop delivery at step 210 the system executes a safety mechanism that enables the system to continue to safely continue automatically delivering medicament with the closed loop delivery algorithm. The safety mechanism can employ any of the methods described herein, either or alone or in any combination with each other. In some embodiments, the system can maintain delivery with the closed loop delivery algorithm according to the safety mechanism until accurate CGM data for a predetermined period of time or a predetermined number of readings is received at step 212 and then terminate the safety mechanism at step 214. In other embodiments, the safety mechanism can be employed for a predetermined period of time and if the accurate CGM data required for operating the closed loop delivery algorithm is not received, closed loop delivery can be terminated or suspended.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357, 603; 10,357,606; 10,492,141; 10/541,987; 10,569,016; and 10,736,037, commonly owned U.S. Patent Publication Nos. 2009/0287180; 2012/0123230; 2013/0053816; 2014/ 0276423; 2014/0276569; 2014/0276570; 2018/0021514; 2018/0071454; 2019/0240398; 2019/0307952; 2019/ 0365997; 2020/0114076; 2020/0206420; 2020/0261644; 2020/0261649; 2020/0306445; and 2020/0329433 and commonly owned U.S. patent application Ser. Nos. 16/879,363; 16/879,927; and Ser. No. 16/920,895.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A system, comprising:
a pump mechanism configured to facilitate delivery of insulin to a user;
a user interface;
a communication element adapted to receive glucose levels from a continuous glucose monitor; and
a processor functionally linked to the pump mechanism, the user interface, and the communication element, wherein the processor is configured to:
automatically calculate insulin doses with a closed-loop delivery algorithm based on glucose levels received from the continuous glucose monitor;
automatically deliver the insulin doses calculated by the closed-loop delivery algorithm to the user with the pump mechanism;
determine that glucose levels are not being received from the continuous glucose monitor;
while the glucose levels are not being received, enable the closed-loop delivery algorithm to continue to automatically calculate insulin doses for automatic delivery with the pump mechanism for a predetermined period of time based on execution of a safety mechanism associated with the closed-loop delivery algorithm, wherein the safety mechanism (i) determines a current glucose value noise based on recent glucose levels received from the continuous glucose monitor and a variance between the glucose levels and predicted glucose levels and (ii) reduces an amount of one or more insulin doses or delays delivery of one or more insulin doses if the current glucose value noise is above a threshold; and
terminate the automatic delivery to the user with the pump mechanism in accordance with a determination that the glucose levels have not been received for a time longer than the predetermined period of time.

2. The system of claim 1, wherein the safety mechanism is a glucose value noise filter.

3. The system of claim 2, wherein the glucose value noise filter is based on one or more of an age of the user, a total daily insulin of the user, a weight predicted insulin action time for the user, and a weight predicted insulin response time for the user.

4. The system of claim 2, wherein the glucose value noise filter is configured to reduce an amount of one or more insulin doses or delay delivery of one or more insulin doses if an amount of noise exceeds a threshold.

5. The system of claim 1, wherein the safety mechanism determines glucose value noise based on a variance between glucose levels.

6. The system of claim 1, wherein the safety mechanism sets a maximum increase in an insulin delivery rate that can be delivered based on the closed-loop delivery algorithm.

7. The system of claim 1, wherein the safety mechanism lowers an aggressiveness of the closed-loop delivery algorithm by reducing automatic correction boluses and increases to basal delivery calculated by the closed-loop delivery algorithm.

8. The system of claim 7, wherein the safety mechanism lowers the aggressiveness of the closed-loop delivery algorithm if the glucose levels were below a low threshold when it was determined that the glucose levels were not being received or that the glucose levels were likely inaccurate.

9. The system of claim 1, wherein the safety mechanism estimates known inaccurate or missing glucose values based on previous or subsequent accurate glucose values.

10. The system of claim 9, wherein the safety mechanism estimates known inaccurate or missing glucose values using linear regression.

11. The system of claim 9, wherein the safety mechanism uses a most recent accurate glucose value in place of known inaccurate or missing glucose values.

12. The system of claim 9, wherein the safety mechanism uses a next subsequent accurate glucose value in place of known inaccurate or missing glucose values.

13. The system of claim 1, wherein the safety mechanism gives less weight to known inaccurate glucose values when calculating insulin doses.

14. The system of claim 1, wherein the safety mechanism is configured to discard known inaccurate glucose levels.

15. The system of claim 14, wherein the safety mechanism is configured to replace discarded known inaccurate glucose values with accurate glucose values.

16. The system of claim 1, wherein the safety mechanism is configured to use past glucose values along with a physiological model to continue automatically delivering insulin doses.

17. The system of claim 1, wherein the safety mechanism is configured to reduce an amount of one or more insulin doses or delay delivery of one or more insulin doses.

18. The system of claim 17, wherein the safety mechanism is configured to review any delayed insulin doses for subsequent delivery upon receiving accurate glucose values.

19. The system of claim 1, wherein the pump mechanism and the processor are disposed within a housing of an ambulatory infusion pump.

20. The system of claim 1, further comprising:
a remote control device for remotely controlling an ambulatory infusion pump including the pump mechanism;
wherein the processor is disposed within the remote control device.

21. A method for delivering insulin, comprising:

receiving glucose levels from a continuous glucose monitor, automatically calculating insulin doses with a closed-loop delivery algorithm based on the glucose levels received from the continuous glucose monitor;

automatically delivering the insulin doses calculated by the closed-loop delivery algorithm to a user;

determining that glucose levels are not being received from the continuous glucose monitor;

while the glucose levels are not being received, enabling the closed-loop delivery algorithm to continue to automatically calculate insulin doses for automatic delivery for a predetermined period of time based on execution of a safety mechanism associated with the closed-loop delivery algorithm, wherein the safety mechanism (i) determines a current glucose value noise based on recent glucose levels received from the continuous glucose monitor and a variance between the glucose levels and predicted glucose levels and (ii) reduces an amount of one or more insulin doses or delays delivery of one or more insulin doses if the current glucose value noise is above a threshold; and terminating the automatic delivery to the user in accordance with a determination that the glucose levels have not been received for a time longer than the predetermined period of time.

* * * * *